US010278814B2

United States Patent
Scorsin et al.

(10) Patent No.: US 10,278,814 B2
(45) Date of Patent: May 7, 2019

(54) HEART VALVE PROSTHESIS (71) Applicant: EPYGON, Paris (FR)

(72) Inventors: Marcio Scorsin, Curitiba (BR); Enrico Pasquino, Marentino—Turin (IT)

(73) Assignee: EPYGON, Paris (FR)

( * ) Notice: Subject to any disclaimer, the term of this patent is extended or adjusted under 35 U.S.C. 154(b) by 65 days.

(21) Appl. No.: 14/396,254

(22) PCT Filed: Apr. 26, 2013

(86) PCT No.: PCT/EP2013/058708
§ 371 (c)(1),
(2) Date: Oct. 22, 2014

(87) PCT Pub. No.: WO2013/160439
PCT Pub. Date: Oct. 31, 2013

(65) Prior Publication Data
US 2015/0088248 A1 Mar. 26, 2015

(30) Foreign Application Priority Data
Apr. 27, 2012 (IT) .............................. TO2012A0372

(51) Int. Cl.
*A61F 2/24* (2006.01)
(52) U.S. Cl.
CPC .......... *A61F 2/2418* (2013.01); *A61F 2/2412* (2013.01); *A61F 2/2415* (2013.01);
(Continued)
(58) Field of Classification Search
CPC .................. A61F 2/2418; A61F 2/2475; A61F 2230/0054; A61F 2220/005;
(Continued)

(56) References Cited

U.S. PATENT DOCUMENTS 4,218,783 A * 8/1980 Reul ...................... A61F 2/2412
137/521
4,759,758 A * 7/1988 Gabbay ................. A61F 2/2412
623/2.13
(Continued)

FOREIGN PATENT DOCUMENTS

CN 1596090 3/2005
CN 101262833 A 9/2008
(Continued)

OTHER PUBLICATIONS

Italian Search Report dated Jan. 21, 2013 issued in Italian Patent Application No. TO2012A000372, 3 pp.
(Continued)

*Primary Examiner* — Seema Mathew
(74) *Attorney, Agent, or Firm* — Nixon & Vanderhye, P.C.

(57) ABSTRACT

Heart valve prosthesis, comprising a ring-shaped supporting structure (3) to be anchored at the valve annulus, and a valve leaflet (5) supported by the supporting structure. The supporting structure comprises a support wall portion (31), at which a root end (51) of the valve leaflet is connected, and a complementary wall portion (32) opposite the support wall portion, which supports a coaptation surface (33) adapted to be sealingly engaged by a free end (52) of the valve leaflet (5), and extending in a direction parallel to the direction of movement of the free end (52) of the valve leaflet (5) at the coaptation surface (33). The free end of the valve leaflet (5) is connected to the support wall portion or to the complementary wall portion by means of a traction member (55), dimensioned in such a way that the free end (52) of the valve leaflet (5) is stopped at the coaptation surface.

21 Claims, 9 Drawing Sheets

(52) U.S. Cl.
CPC ............... *A61F 2220/0075* (2013.01); *A61F 2230/0034* (2013.01); *A61F 2230/0054* (2013.01); *A61F 2240/001* (2013.01); *A61F 2250/0096* (2013.01); *Y10T 29/49838* (2015.01)

(58) Field of Classification Search
CPC ...... A61F 2220/0058; A61F 2220/0075; A61F 2230/0008; A61F 2002/068; A61F 2220/0008; A61F 2220/0016; A61F 2/2412; A61F 2/2457; A61F 2/24; A61F 2250/0003; A61F 2/246; A61F 2/2454
See application file for complete search history.

(56) References Cited

U.S. PATENT DOCUMENTS

| | | | |
|---|---|---|---|
| 4,960,424 A | 10/1990 | Grooters | |
| 5,314,467 A | 5/1994 | Shu | |
| 6,719,788 B2 | 4/2004 | Cox | |
| 6,780,200 B2 | 8/2004 | Jansen | |
| 7,591,847 B2* | 9/2009 | Navia | A61F 2/2412 623/2.1 |
| 8,403,979 B2* | 3/2013 | Paul, Jr. | A61F 2/2412 623/1.24 |
| 9,375,312 B2* | 6/2016 | Weber | A61F 2/2418 |
| 2003/0199975 A1* | 10/2003 | Gabbay | A61F 2/2445 623/2.36 |
| 2004/0122513 A1* | 6/2004 | Navia | A61F 2/2412 623/2.12 |
| 2004/0210303 A1 | 10/2004 | Sedransk | |
| 2005/0038508 A1* | 2/2005 | Gabbay | A61F 2/2445 623/2.36 |
| 2005/0070999 A1* | 3/2005 | Spence | A61F 2/2418 623/2.37 |
| 2005/0075727 A1* | 4/2005 | Wheatley | A61F 2/2412 623/2.17 |
| 2006/0195182 A1* | 8/2006 | Navia | A61F 2/2412 623/2.16 |
| 2006/0259135 A1* | 11/2006 | Navia | A61F 2/2409 623/2.11 |
| 2007/0005134 A1* | 1/2007 | McCarthy | A61F 2/2409 623/2.17 |
| 2007/0156229 A1* | 7/2007 | Park | A61F 2/07 623/1.15 |
| 2007/0270943 A1* | 11/2007 | Solem | A61B 17/0401 623/2.11 |
| 2007/0288086 A1* | 12/2007 | Kalmann | A61F 2/2418 623/1.24 |
| 2008/0125860 A1* | 5/2008 | Webler | A61B 17/00234 623/2.36 |
| 2009/0132036 A1* | 5/2009 | Navia | A61F 2/2445 623/2.36 |
| 2009/0281618 A1 | 11/2009 | Hill et al. | |
| 2009/0292353 A1* | 11/2009 | Yoganathan | A61B 17/00234 623/2.11 |
| 2010/0082094 A1 | 4/2010 | Quadri et al. | |
| 2010/0152835 A1* | 6/2010 | Orr | A61F 2/07 623/1.15 |
| 2010/0210899 A1* | 8/2010 | Schankereli | A61B 17/00234 600/37 |
| 2010/0256743 A1* | 10/2010 | Hinchliffe | A61F 2/2418 623/1.24 |
| 2011/0208297 A1 | 8/2011 | Tuval et al. | |
| 2011/0319989 A1* | 12/2011 | Lane | A61F 2/2418 623/2.11 |
| 2012/0197388 A1* | 8/2012 | Khairkhahan | A61F 2/246 623/2.11 |
| 2014/0031857 A1* | 1/2014 | Richardson | A61F 2/013 606/200 |
| 2015/0351908 A1* | 12/2015 | Keranen | A61F 2/2466 623/2.37 |
| 2016/0089234 A1* | 3/2016 | Gifford, III | A61F 2/2445 623/2.18 |
| 2016/0143736 A1* | 5/2016 | Vidlund | A61B 17/0057 623/2.4 |
| 2017/0065409 A1* | 3/2017 | Scorsin | A61F 2/2412 |
| 2017/0312077 A1* | 11/2017 | Vidlund | A61B 17/0401 |
| 2018/0289484 A1* | 10/2018 | Kofidis | A61F 2/2412 |
| 2019/0000621 A1* | 1/2019 | Wilson | A61F 2/2445 |

FOREIGN PATENT DOCUMENTS

| | | |
|---|---|---|
| CN | 102083391 | 1/2011 |
| EP | 0 183 904 | 6/1986 |
| EP | 0 183 904 A2 | 6/1986 |
| EP | 0 183 904 A3 | 6/1986 |
| EP | 0 532 62737378 B1 | 5/1996 |
| UA | 27373 C2 | 9/2000 |
| UA | a200902801 | 10/2009 |
| WO | WO 03/037227 | 5/2003 |
| WO | WO 2004/093726 | 11/2004 |
| WO | 2007/024755 A1 | 3/2007 |
| WO | 2009/132187 A1 | 10/2009 |
| WO | WO 2009/132187 | 10/2009 |

OTHER PUBLICATIONS

Intellectual Property Office of Singapore Invitation to Respond to Written Opinion, Search Report and Written Opinion dated Oct. 1, 2015, issued in corresponding Patent Application No. 11201406936P, 11 pages.
Perier, Patrick, et al., "Toward a New Paradigm for the Reconstruction of Posterior Leaflet Prolapse: Midterm Results of the "Respect Rather Than Resect" Approach," The Society of Thoracic Surgeons, 2008, vol. 86, No. 3, pp. 718-725.
Chinese Official Action dated Aug. 28, 2015 and its translation.
International Search Report for PCT/EP2013/058708 dated Jul. 19, 2013.
Written Opinion of the International Searching Authority for PCT/EP2013/058708 dated Jul. 19, 2013.
A. Carpentier, "Cardiac Valve Surgery—the French Correction", The Journal of Thoracic and Cardiovascular Surgery, vol. 86, No. 3, 1986, pp. 323-337.
P. Perier et al., "Toward a New Paradigm for the Reconstruction of Posterior Leaflet Prolapse: Midterm Results of the "Respect Rather than Resect", Approach", The Annals of Thoracic Surgery, vol. 86, No. 3, Sep. 2008, pp. 718-725.
Butany, J., et al., "Analysis of prosthetic cardiac devices: a guide for the practising pathologist," J Clin Pathol, Dec. 31, 2005, vol. 58, pp. 113-124.
Patent Examination Report No. 1 dated Nov. 16, 2016, issued in Australian Patent Application No. 2013254678.
Office Action dated Mar. 1, 2017, issued in Canadian Patent Application No. 2,870,791.
The Fourth Office Action dated Mar. 14, 2017, issued in Chinese Patent Application No. 2013800334487 and English translation.
Notice of Reasons for Rejection dated Jan. 4, 2017, issued in Japanese Patent Application No. 2015-507551 and English translation.
Notice Prior to Examination dated May 7, 2017, issued in Israeli Patent Application No. 235285 and English translation.
Office Action dated Nov. 16, 2016, issued in Mexican Patent Application No. Mx/a/2014/012950.
Office Action dated May 3, 2017, issued in Mexican Patent Application No. Mx/a/2014/012950.
Invitation to Respond to Written Opinion dated Jul. 7, 2016, issued in Singapore Patent Application No. 11201406936P.
Preliminary Results of Examination as to Substance dated Feb. 27, 2017, issued in Ukrainian Patent Application No. a 2014 12688 and English translation.
Decision on Grant a Patent for Invention dated Jun. 2, 2017, issued in Ukrainian Patent Application No. a 2014 12688 and English translation.

(56) References Cited

OTHER PUBLICATIONS

The Second Office Action dated Apr. 11, 2016, issued in Chinese Patent Application No. 201380033448.7, and English translation.
The Third Office Action dated Sep. 30, 2016, issued in Chinese Patent Application No. 201380033448.7, and English translation.
Office Action dated Feb. 1, 2017, issued in Russian Patent Application No. 2014145477/14(073347), and English translation.
Carpentier, Alain, "Cardiac valve surgery—the "French correction,"" The Journal of Thoracic and Cardiovascular Surgery, vol. 86, No. 3, Sep. 1983, pp. 323-337.
Bortolotti et al., "The Meadox-Gabbay Pericardial Xenograft: Failure of the Unicusp Principle," The Annals of Thoracic Surgery, 1992, vol. 54, No. 5, pp. 952-957.
Dasi et al., "Hemodynamic Energy Dissipation in the Cardiovascular System: Generalized Theoretical Analysis on Disease States," Annals of Biomedical Engineering, Biomedical Engineering Society, vol. 37, No. 4, Feb. 18, 2009, pp. 661-673.
Faludi et al., "Left ventricular flow patterns in healthy subjects and patients with prosthetic mitral valves: An in vivo study using echocardiographic particle image velocimetry," Journal of Thoracic and Cardiovascular Surgery, vol. 139, No. 6, Jun. 2010, pp. 1501-1510.
Jeevan et al., "Engineering challenges and the future prospects of transcatheter mitral valve replacement technologies: a comprehensive review of case studies," Expert Review of Medical Devices, vol. 14, No. 4, 2017, pp. 297-307, https://doi.org/10.1080/17434440.2017.1305267.
Kilner et al., "Asymmetric redirection of flow through the heart," Nature, vol. 404, No. 6779, Apr. 13, 2000, pp. 759.
Kim et al., "Left Ventricular Blood Flow Patterns in Normal Subjects: A Quantitative Analysis by Three-Dimensional Magnetic Resonance Velocity Mapping," Journal of the American College of Cardiology, Jul. 1995, vol. 26, No. 1, pp. 224-238.
Klabunde, "Cardiovascular Physiology Concepts," 2nd Edition, Publisher Wolters Kluwer, Lippincott Williams & Wilkins, ISBN 978-1-4511-1384-6, 2005, pp. 93-105.
Klingensmith et al., "The Washington Manual of Surgery," Washington University School of Medicine, 5th Edition, 2008, Publisher Lippencott Williams & Wilkins, ISBN 978-0/7817-7447-5, pp. 512 Table 30-1.
Singhal et al., "Bioprosthetic Heart Valves: Impact of Implantation on Biomaterials," ISRN Biomaterials, vol. 2013, Hindawi Publishing Corporation, Article ID 728791, http://dx.doi.org/10.5402/2013/728791.

\* cited by examiner

HEART VALVE PROSTHESIS

This application is the U.S. national phase of International Application No. PCT/EP2013/058708 filed 26 Apr. 2013 which designated the U.S. and claims priority to Italian Patent Application No. TO2012A000372, filed 27 Apr. 2012, the entire contents of each of which are hereby incorporated by reference.

The present invention relates to a heart valve prosthesis, comprising a ring-shaped supporting structure to be anchored at the valve annulus, and a valve leaflet of flexible material floatingly supported by said supporting structure.

In the mitral valve, the anterior leaflet of the valve covers the space between the valve commissures (including the trigones) and is in direct fibrous continuity with the aortic annulus under the left and non-coronary cusps of the aortic valve, including the fibrous trigone between the left and non-coronary cusps of the aortic valve. Thin bundles of collagen fibres resembling tendons extend circumferentially from each fibrous trigone for a variable distance towards the corresponding side of the mitral orifice. The posterior half to two thirds of the annulus supporting the posterior leaflet is mainly muscular, with little or no fibrous tissue. This muscle is mainly positioned perpendicularly to the annulus, and a less conspicuous group of muscle fibres is located parallel to the annulus.

The mitral annulus corresponds to the transition between the endocardial layer of the left atrium, the valve tissue and the endocardium and myocardium of the left ventricle.

The orifice area of the mitral valve at the annulus is approximately 6.5 $cm^2$ in women and 8 $cm^2$ in men. The circumference is approximately 9 cm in women and 10 cm in men. Depending on the inotropic state of the heart, the difference between the diastolic and systolic size of the annulus varies from 23% to 40%. The effective area of the valve orifice is approximately 30% smaller than the size of the annulus.

Although solutions have been proposed for the percutaneous transcatheter implantation of artificial aortic valves, the distinctive characteristics of the mitral valve have hitherto prevented the development of equally effective mitral valve prostheses.

The following considerations must be borne in mind when designing a device for replacing the mitral valve:

Degenerative disease: mitral valve prolapse is the most common pathological condition found in heart valves, and is present in about 2% of the population; 5% of these develop mitral insufficiency. Mitral prolapse is a degenerative pathology in which calcification of the annulus is encountered in rare cases. This is one of the main differences between aortic and mitral pathologies, since the mitral ring is larger and more elastic, and these two characteristics make it difficult to anchor a percutaneous device.

Shape of the mitral valve: the annulus and valve are asymmetric, with a long axis of about 5 cm between the commissures and a short axis of 4 cm in the antero-posterior direction in systole (generally with a long axis to short axis ratio of 4/4 to 3/4) when the valve is closed, because of the D shape of the valve. During diastole, the annulus moves outwards with the posterior wall of the left ventricle, allowing the mitral orifice to become more circular. When degenerative pathological dilation of the annulus is present, the shape of the annulus becomes more circular throughout the cardiac cycle, principally as a result of an increase in the posterior part of the annulus. This leads to a change in the diameters of the mitral annulus. The short axis (antero-posterior diameter) is elongated, causing the shape of the valve to become more circular, thereby preventing perfect coaptation of the two leaflets and aggravating the mitral insufficiency. Although commercially available mitral prostheses are circular, in a percutaneous device this may give rise to problems of coaptation (intraprosthetic insufficiency) and/or perivalvular leakage.

Pressure of the left ventricle: when the left ventricle contracts, the intraventricular pressure forces the mitral valve to close, the valve being subjected to the effects of systolic stress. Systolic stress is significantly greater than diastolic stress (aortic valve); it is therefore important to have perfect coaptation in a device intended for the mitral position.

Obstruction of the left ventricle outflow tract: when the mitral valve is surgically replaced the anterior leaflet is completely excised. One of the major issues related to a percutaneous implant of a mitral valve prosthesis is that the anterior leaflet can not be excised. The retaining leaflet can lead to a potential obstruction of the left ventricle outflow tract when pushed into the ventricle by the prosthesis. The bigger the size of the valvular prosthesis, the higher is the risk of obstruction as the leaflet is pushed further into the ventricle.

Patients with mitral (annuloplasty) rings: patients who have already undergone a mitral repair operation may develop recurrent insufficiency. Circular artificial tricuspid aortic valves do not operate correctly in patients with D-shaped mitral rings, since they do not allow perfect coaptation of the three leaflets; furthermore, owing to the deformation of the structure, perivalvular leakage occurs, due to the lack of coupling between the circular and the D shape, as well as reduced stability of the implant with a risk of migration of the prosthesis.

For the reasons stated above, there are major constraints on the use of e.g. aortic percutaneous or sutureless valve implant systems in mitral position. Valve replacement by the percutaneous route or by minimally invasive surgery is becoming an increasingly common practice for the aortic and pulmonary valves, but cannot be used as yet for the mitral valve.

As explained above, the mitral annulus differs from the aortic annulus in not being circular, especially in a patient with a mitral annuloplasty ring. The available transcatheter prostheses are always tricuspid, and if they are not perfectly circular after expansion (due to an irregular expansion of the stent) they tend to reduce the degree of coaptation of the valve leaflets, resulting in prosthetic insufficiency. Since the aortic annulus is practically circular, transcatheter valves almost always work well, unless the stent is distorted during implantation owing to the presence of dystrophic calcification of the annulus and the valve leaflets. The risk of insufficiency in the mitral position, which is not circular, is very considerable, since the mitral annulus does not offer any resistance during the expansion of the prosthesis, thus leading to over-dilation and consequent loss of coaptation between the three valve leaflets.

One object of the present invention is to provide a heart valve prosthesis which can at least partially overcome the problems of the prior art described above.

The aforesaid object is achieved according to the invention with a heart valve prosthesis of the type defined initially, wherein said supporting structure comprises a support wall portion at which a root end of the valve leaflet is connected, and a complementary wall portion opposite said support wall portion, which supports a static or quasi-static coaptation surface adapted to be sealingly engaged by a free end of the valve leaflet, and extending in a direction substantially parallel to the direction of movement of the free end of the valve leaflet at the coaptation surface; and said free end of the valve leaflet is connected to said support wall portion or to said complementary wall portion preferably in their lateral portions by means of at least one traction member of flexible material, dimensioned to such a length that the movement of the free end of the valve leaflet is stopped at said coaptation surface. The invention was developed on the basis of an examination of the prior art in the field of heart valve repair.

As explained by Carpentier, the aim of mitral valve repair is to restore a good coaptation surface in order to provide satisfactory mitral valve function (Carpentier A. Cardiac valve surgery—the "French correction." J Thorac Cardiovasc Surg 1983; 86: 323-37). Conventionally, the repair of a posterior leaflet prolapse consists in the resection of the leaflet followed by annuloplasty using a ring, and this has been shown to have excellent long-term durability. Typically, echocardiographic findings after mitral valve repair show a posterior leaflet with reduced mobility or no mobility at all, which hangs vertically from the annulus and forms, as demonstrated experimentally and clinically (Cohn, L. H., Couper, G. S., Aranki, S. F., et al. Long-term results of mitral valve reconstruction for regurgitation of the myxomatous mitral valve. J Thorac Cardiovasc Surg 1994; 107: 143-51), a support against which the anterior leaflet bears in apposition. These conclusions were developed further by Perier (Perier, P., Hohenberger, W., Lakew, F., Batz, G., Urbanski, P., Zacher, M., and Diegeler, A. Toward a new paradigm for the reconstruction of posterior leaflet prolapse: midterm results of the "respect rather than resect" approach. Ann Thorac Surg 2008 September; 86(3): 718-25), who deliberately converted the bicuspid mitral valve into a monocuspid valve by the apposition of the anterior leaflet on an extended coaptation surface formed on the verticalized posterior leaflet.

The concept on which the invention is based, therefore, is that of a single extended leaflet coapting on a wall which supports an extended, smooth, regular and substantially vertical coaptation surface, thus reducing the risk of intraprosthetic regurgitation. Additionally, the edge of the leaflet is retained by a traction member which simulates a system of chordae tendineae.

Because only one leaflet is present, a larger moving surface is subjected to the pressures created by the cardiac cycle. This results in faster opening and closing of the valve by comparison with tricuspid valves. Furthermore, using a monocuspid valve could reduce the incidence of calcification phenomena. Indeed, it is known that, in some devices of the tricuspid type, fibrosis of the valve leaflets occurs, sometimes with the formation of intrinsic and extrinsic dystrophic calcification, in the less mobile part of the leaflet. We may deduce from this that the continual movement of the single leaflet could contribute to the prevention of fibrosis and calcification of the tissue (Gabbay, S., Bortolotti, U., Cipolletti, G., Wasserman, F., Frater, R. W., and Factor, S. M. The Meadox unicusp pericardial bioprosthetic heart valve: new concept. Ann Thorac Surg 1984 June; 37(6): 448-56).

The supporting structure preferably has a D-shaped cross section in a plane perpendicular to the axis of the structure, i.e. the axis corresponding to the direction of flow of blood when the supporting structure is implanted.

D shape as used herein are any shapes which comprise a two parts one of which is bent in about circular manner whereas the other part is substantially straight or bent to a less degree on either side, respectively.

The straight part might also be bent slightly after implantation. With the bending of the straight part "in vivo" the native leaflet can be pulled upwards with respect of the blood flow. Further, the portion shows better anchoring conditions after the bending.

The substantially straight part preferably is the support wall portion and the bent part preferably is the complementary wall portion comprising the coaption surface.

Alternatively, the straight part is the complementary wall portion comprising the coaption surface and the bent part is the support wall portion.

The cross section of the mitral valve annulus has a D shape. A supporting structure with a D shape therefore provides a better fitting between the annulus and the supporting structure as there is contact between the annulus and the supporting structure substantially all around the supporting structure. The better fitting and contacting between the support structure and the annulus result e.g. in better stability of the implant as well as a reduced risk of perivalvular leakage. Further, the aortic annulus is not compressed as a result of an implantation of a mitral prosthesis, as there is no expansion of the mitral annulus with a D shaped supporting structure, especially no expansion of the mitral annulus in the direction of the aortic annulus therefore on the anterior side.

The anterior side of the supporting structure is the side which is arranged next to the aortic annulus when implanted. The anterior side preferably is the complementary wall portion. The posterior side is opposite of the anterior side and therefore at maximum distance to the aortic annulus when implanted. The posterior side preferably is the support wall portion.

The dimensions of the support structure are preferably such that a distance perpendicular to the anterior-posterior distance is preferably about a factor from 1.1-1.3, more preferably about a factor 1.2, longer than the anterior-posterior distance. The axial length of the support structure is preferably about 32 mm and the thickness of the wall as well as the width of struts is preferably about 500 μm (micrometer).

In a preferred variation, the inflow end and the outflow end are flared outwardly with respect to the flow direction and the cardiac wall. The inflow end is preferably flared about 20° to 40°, more preferably about 30°, with respect to the flow direction and the outflow end is preferably flared about 7.5° up to 17.5°, more preferably about 10°, with respect to the flow direction.

In an alternative embodiment, the ends of the prosthesis are asymmetrically flared such that the anterior side has a different flare than the posterior side. The anterior side in the variation preferably is flared at the outflow end preferably about 7.5° to 17.5°, more preferably about 10°, with respect to the axis and flared at the inflow end preferably about 15° to 25°, more preferably about 20°, with respect to the axis whereas the posterior side is flared at the outflow end, preferably about 7.5° to 17.5°, more preferably about 10°, with respect to the axis and at the inflow end about 20° to 40°, more preferably about 30°, with respect to the axis. The asymmetric flare might be present in combination with the various prosthesis of the invention described herein.

In a further alternative embodiment, the flares might be provided as curvilinear flares. Curvilinear flares mean in that the flares are bent in a kind of circular, convex manner with respect to the axis so that the flare bends outwardly first and at least slightly inwardly on towards the inflow end or the outflow end, respectively, with respect to the axis. The curvilinear flares might be present in combination with the various prosthesis of the invention described herein.

The flares provide a force of the support structure on the atrio-ventricular junction and surrounding tissues of the posterior ventricular wall which keeps the fixation of the support structure in the annulus. A smaller flare at the outflow end of the anterior portion than on the posterior portion helps minimizing the risk of obstructing the left outflow tract.

In another variation of the prosthesis, the supporting structure has an asymmetric arrangement in the axial direction such that one side, preferably the anterior side is shorter than an opposite side in axial direction, preferably the posterior side.

The asymmetric arrangement is preferably constructed such that the anterior portion is as short such that the native leaflet is basically not pushed outwards in the left ventricle. In the left ventricle the native leaflet could interfere with the blood outflow through the aorta in systole.

The native leaflets are not excised when an off-pump procedure is performed. The native leaflets are rather pushed to the side, therefore out of the opening, with the prosthesis such as to not interfere with the blood flow. However, with an anterior portion having a certain length, the anterior native leaflet might be pushed in the left ventricle. When the heart contracts during systole to push the blood out of the aorta, the anterior native leaflet might block some of the blood flow through the aorta when covering some parts of the aortic annulus. With a shorter anterior portion, the anterior leaflet is not pushed into the left ventricle outflow tract but rather moves towards the inflow tract.

The asymmetric construction might be part of any prosthesis discussed herein.

It is also possible that the anterior and posterior portions are the same length.

In any prosthesis the valve and the at least one traction member might be constructed as a single piece, preferably as a single piece made of pericardium.

The traction member and the valve might be cut out of pericardium as one piece. With a construction as one piece, there is no need to attach the traction member to the valve leaflets. A construction without an attachment is more stable than a two piece construction. Therefore, the risk of a malfunction is reduced.

It is also possible to construct the traction member and the valve as two or more pieced arrangements.

Pericardium has been shown to be persistent and therefore well suited for the purpose as valve and traction member. It is also possible to use other biocompatible materials such as biocompatible plastics or tissues.

The at least one traction member is preferably attached to lateral portions of the supporting structure.

The lateral portions are the two sides of the supporting structure which include the utmost ends of the anterior side and the posterior side. The anterior side and the posterior side preferably relate to the complementary wall portion and the support wall portion. The attachment of the traction member can be anywhere along the lateral portions.

When the traction members are arranged at the lateral portions, their interference with the movement of the valve is minimized as the valve leaflet preferably opens in an anterior posterior direction.

The invention further comprises a delivery device comprising a prosthesis according to the invention described herein.

Further, the invention relates to a method for manufacturing a heart valve prosthesis, preferably a prosthesis according the invention described herein, comprising the steps of
providing a support structure, preferably a D-shaped support structure with a support wall portion and a complementary wall portion,
assembling a valve leaflet of flexible material in the support structure,
wherein the valve leaflet is connected with a root end to the support wall or the complementary wall, preferably through stitching,
and a free end of the valve is attached to the other wall portion, complementary wall portion or support wall portion through a traction member.

In the method of manufacturing the valve and the traction member are preferably constructed as a single piece.

Although the characteristics and advantages of the prosthesis according to the invention are discussed herein with regard to mitral valve replacement, it will be clear that the inventive concept can also be applied to valve prostheses intended for the replacement of other heart valves.

Further characteristics and advantages of the prosthesis according to the invention will be made clear by the following detailed description, which refers to the attached drawings, provided purely by way of non-limiting example, in which:

FIG. 3 is a plan view (showing the inflow side) of the valve prosthesis of FIG. 1a;

With reference to FIGS. 1 to 4, a heart valve prosthesis according to the invention, shown schematically, is indicated as a whole by 1. This prosthesis 1 comprises a ring-shaped supporting structure 3 to be anchored at the valve annulus, which may already have been repaired with an annuloplasty ring. With respect to the direction perpendicular to the cross section of the ring, the supporting structure 3 has an inflow side or end 3b and an outflow side or end 3a. In this context, the terms "inflow" and "outflow" refer to the inflow and outflow of the blood into and from the valve when the prosthesis is in use.

In plan view (FIG. 3), the illustrated valve is D-shaped, making it suitable for implants in the atrio-ventricular position (mitral or tricuspid). In an alternative embodiment which is not shown, the valve according to the invention may have a circular shape suitable for implants in the aortic or pulmonary position.

Figure 1A:
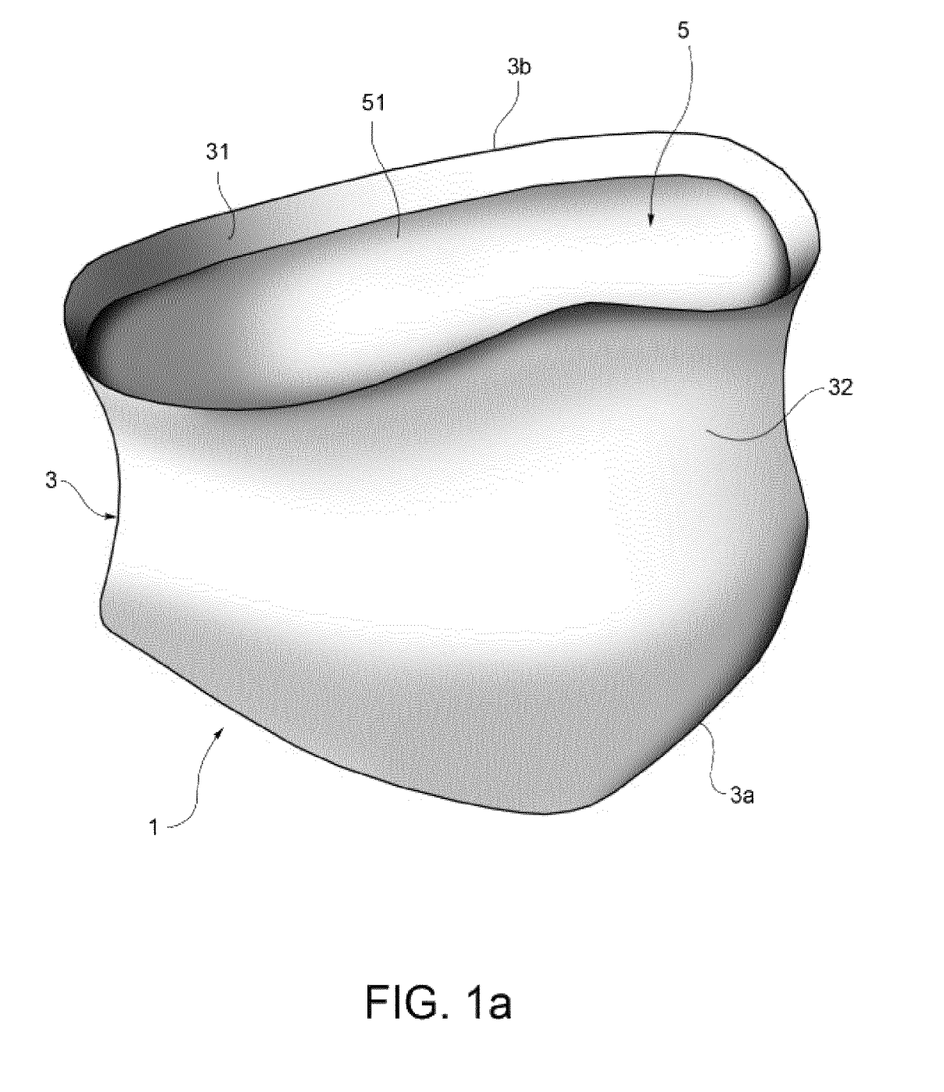
FIG. 1a shows a simplified perspective view from above of a valve prosthesis according to the invention.
Figure 1B:
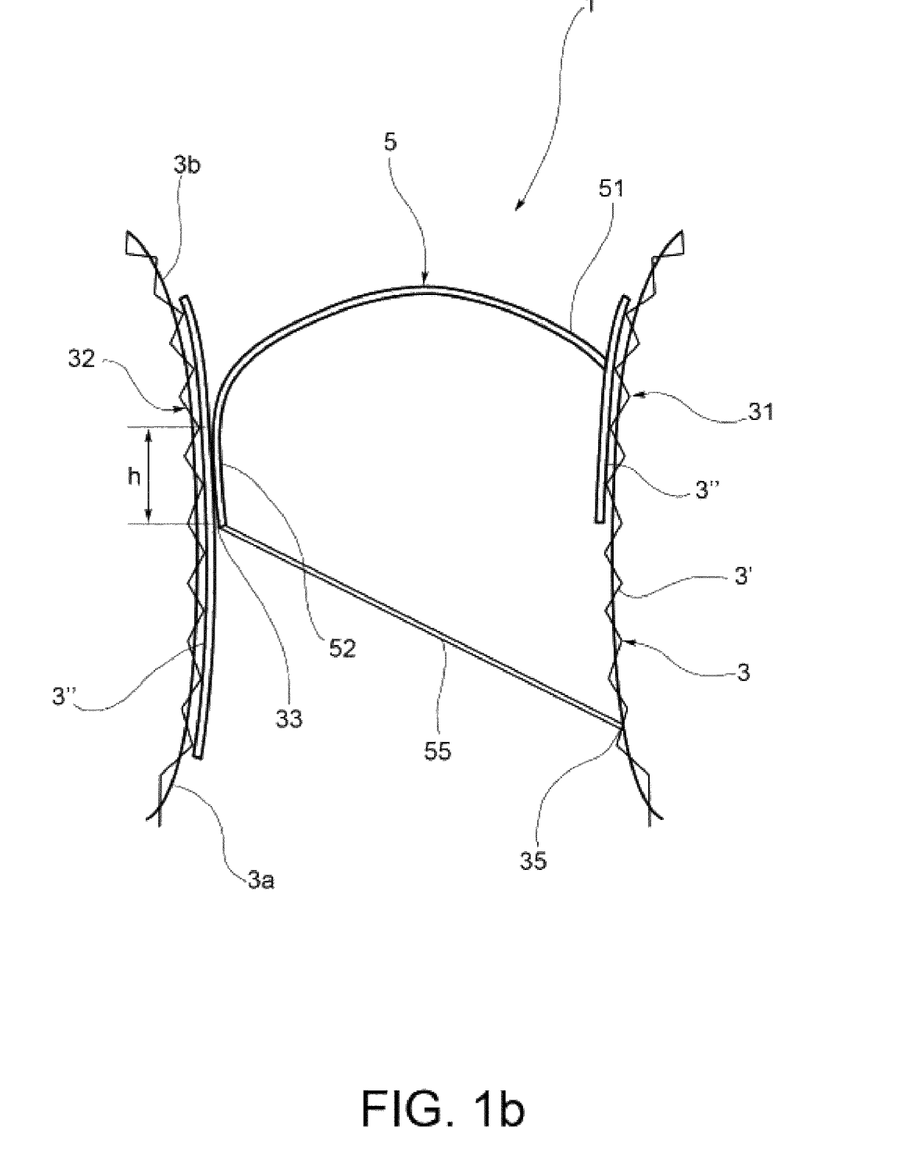
FIG. 1b shows a simplified schematic view in cross section (A2-P2 according to Carpentier) of a valve prosthesis according to the invention.

Preferably, as shown schematically in FIG. 1b, the supporting structure 3 comprises a skeleton 3' formed by a valve stent, which can assume a positioning configuration in which the stent is folded to allow it to be positioned through a catheter, and an implant configuration, in which the stent is expanded to be adapted and anchored to the valve annulus. In order to achieve this expansion in position, the material of the stent may be a self-expanding material, for example a shape memory alloy, or a shaped balloon associated with the positioning system may be provided, this balloon being inflated to cause the expansion of the stent. The aforesaid expansion may also provide a change in the shape of the prosthesis, particularly in order to create the D shape of the mitral or tricuspid valve.

More specifically, the prosthesis according to the positioning system may be transferred to the implantation site by an on-pump, sutureless surgical procedure, by an off-pump surgical procedure with transatrial or transapical access through a mini-thoracotomy, or, last but not least, by an intervention procedure with percutaneous access.

The release of the prosthesis from the positioning system can take place in a single action or can be a two step procedure. In a first step, a portion of the prosthesis (either the inflow or the outflow portion, depending on the implantation method and the visualization procedure) is released, so that its vertical and horizontal positioning can be adjusted. In the second step, the second portion of the prosthesis is released (complete release).

Preferably, the valve prosthesis is of the sutureless type; that is to say, no stitches are required to anchor it to the valve seat. For this purpose, the supporting structure 3 may be anatomically shaped so as to be anchored securely to the valve annulus, or can be provided with special-purpose formations for anchoring.

More specifically, the outer portion of the valve stent which comes into direct contact with the native fibrous annulus may be slightly concave in order to follow the contour of the annulus and facilitate anchoring thereto. The structure of the valve stent in this area may also include anchorages formed by grafts integrated into the structure itself. Other possibilities to support the anchor are hooks or struts. This method of anchoring makes it possible to avoid the progressive dilation of the fibrous annulus, thus reducing the risk of perivalvular leakage and detachment of the prosthesis. The anchoring takes place jointly with the opening of the atrial and ventricular portions of the valve stent.

Preferably, the atrial (inflow) portion of the valve stent has a special collapsible mesh design like the rest of the stent, and at the end of the opening of the prosthesis it assumes an outwardly flared shape such that secure contact can be established with the atrial (inflow) wall. The purpose of this portion of the prosthesis is to ensure the positioning of the prosthesis by means of progressive colonization by fibrous tissue (fibrous pannus). The profile of the atrial (inflow) portion is higher in the posterior anatomical portion and lower in the anterior portion, the aim being in the latter case to reduce any possible interference with the aortic valve. This structure may be made of metal alloy only, or may be covered with biological or synthetic tissue in order to optimize colonization by the fibrous tissue.

Preferably, the ventricular (outflow) portion of the valve stent has a special collapsible mesh design like that of the atrial (inflow) portion. The profile is markedly asymmetric. The posterior ventricular (outflow) portion has a marked protrusion, which not only provides contact with the posterior ventricular (outflow) wall, but also provides a member for anchoring to the support (chordae) of the anterior monocuspid valve leaflet and to the chordae of any posterior leaflet, as described below. It may take the form of a single structure or two or three separate structures. The anterior ventricular (outflow) part has a low profile and is given a flared shape to promote the anchoring of the prosthesis to the ventricle without interfering with the mitral-aortic continuity, in order to avoid creating compression which would lead to conduction disturbances. The anterior ventricular side of the stent in its more distal portion could have an everting angle close to 180°. Therefore, the stent could be originally symmetric D shape and after thermal shaping only the anterior ventricular part could evert becoming asymmetric. This condition could imply the grabbing of the edge of the native anterior leaflet and the native leaflet in the direction of the atrium, letting the left ventricle outflow tract free. Further, anchoring of the anterior ventricular portion is improved with an everted ventricular part. The ventricular (outflow) portion of the stent may be made of metal alloy only, or may be covered with biological or synthetic tissue in order to optimize colonization by the fibrous tissue.

As a general rule, the supporting structure 3 of the valve prosthesis may have a coating 3", of pericardium for example, or of biological tissue in general, or of synthetic tissue, covering some or all of the supporting structure. The coating 3" is particularly necessary if the supporting structure is a valve stent 3', in order to provide a seal at the valve annulus to which the prosthesis is fitted.

The valve prosthesis further comprises a single valve leaflet 5 of flexible material supported floatingly by the supporting structure 3. The flexible material of the valve leaflet must have characteristics meeting the requirements of cyclic fatigue resistance. The valve leaflet 5 may be made of pericardial tissue, or biological tissue in general, or synthetic tissue. The pericardial tissue, in addition to the conventional cross-link tissue fixation, should preferably be subjected to chemical treatment serving to provide long-term retardation of the dystrophic calcification of the biological tissue. The valve leaflet may be made as a kind of extension of the material which coats the supporting structure 3 of the prosthesis, or as a separately produced part which is subsequently anchored to the support wall portion 31 of the supporting structure 3. In a plan view (FIG. 3), the surface extension of the valve leaflet 5 in the example of FIGS. 1 to 4 is substantially equal to the cross section of the orifice delimited by the supporting structure 3.

In relation to this valve leaflet, the supporting structure 3 comprises a support wall portion 31 at which a root end 51 of the valve leaflet 3 is connected. For this purpose, the outflow portion 3b of the valve stent has a valve support for the valve leaflet of the prosthesis. This support is integrated into the structure of the stent, and is designed to withstand cyclic fatigue stress, to provide adequate support for the valve leaflet, and to allow the prosthesis to be fully collapsed for insertion into the positioning system.

The supporting structure 3 further comprises a complementary wall portion 32 connected to and opposite the support wall portion 31, which supports a coaptation surface 33 (visible in FIGS. 1b and 4) adapted to be sealingly engaged by a free end 52 of the valve leaflet 5. In the example shown in FIGS. 1 to 4, the coaptation surface 33 is static, in the sense that it is integral with the supporting structure 3 of the valve prosthesis. In particular, in the example of FIGS. 1 to 4, the coaptation surface 33 is defined by an inner face (that is to say, a face turned towards the centre of the valve prosthesis) of the complementary wall portion 32 of the supporting structure 3. At the coaptation surface, the complementary wall portion 32 of the supporting structure 3 has the coating discussed above.

If the valve prosthesis in question is a mitral prosthesis, the support wall portion 31 of the supporting structure 3 is an anterior wall portion of this supporting structure, while the complementary wall portion 32 is a posterior wall portion. The terms "anterior" and "upper" refer to the positioning of the valve prosthesis in use, at the mitral annulus.

In use, the valve leaflet 5, being flexible and connected to the supporting structure 3 by its root end 51, is able to bend with respect to its root end 51, under the action of the blood pressure present upstream and downstream of the valve prosthesis, thereby opening or closing the orifice formed by the supporting structure 3 of the valve prosthesis. In the closed position, the edge of the free end 52 of the valve leaflet 5 engages the coaptation surface 33 positioned on the complementary wall portion 32 of the supporting structure 3.

The coaptation surface 33 extends in a direction substantially parallel to the direction of movement of the free end 52 of the valve leaflet 5 at the coaptation surface 33. When the valve prosthesis is in use, the aforesaid direction is substantially vertical. Thus it is possible to obtain a large coaptation surface, similar to that achieved with the Perier method for creating a mitral annuloplasty; the coaptation surface may have an extension h (see FIG. 1*b*) of at least 5 mm in the direction of movement of the free end 52 of the valve leaflet. Consequently, the possibility of regurgitation if the prosthesis becomes deformed is reduced.

Figure 2:
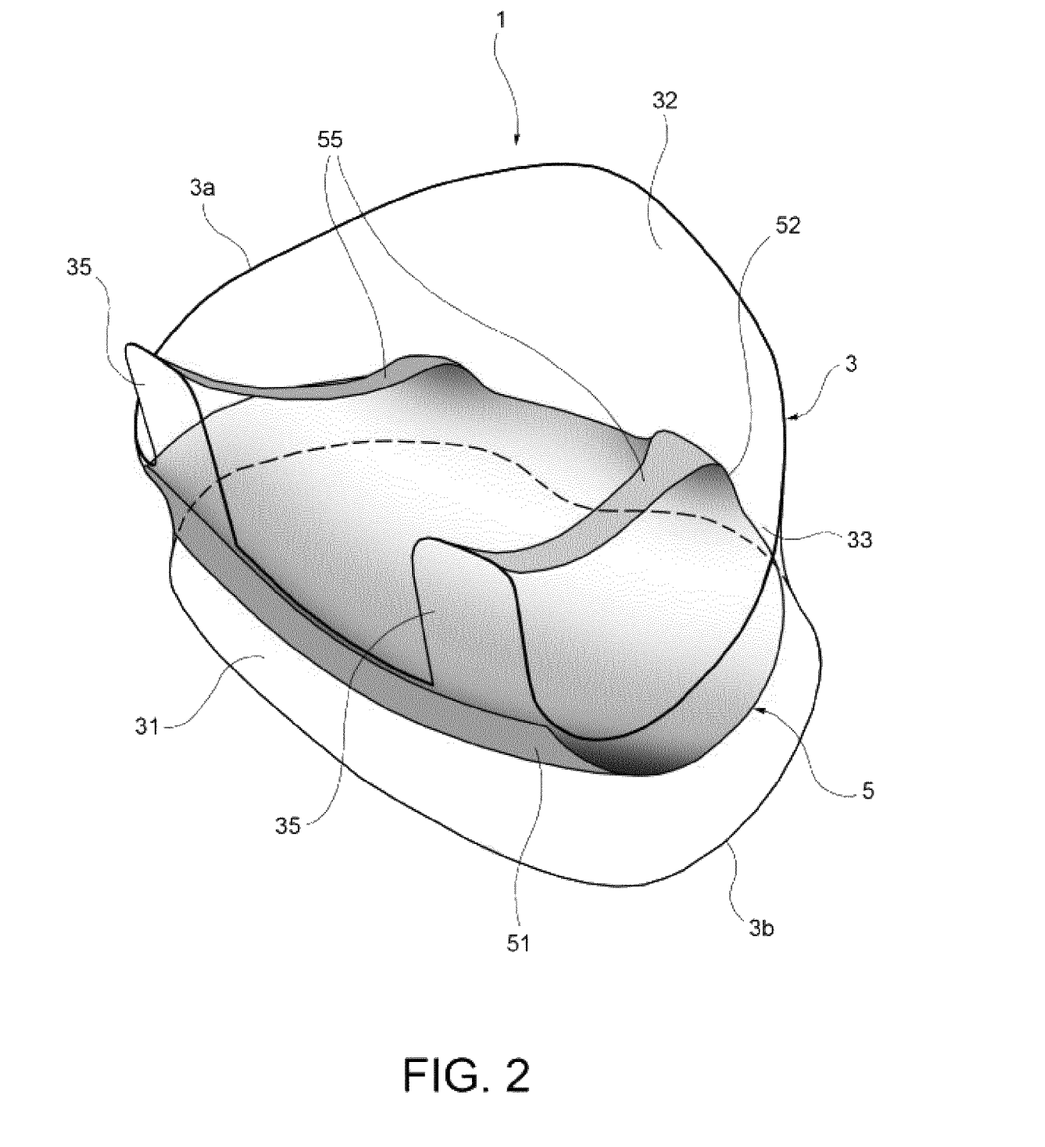
FIG. 2 is a perspective view from below (showing the outflow side) of the valve prosthesis of FIG. 1a; for greater clarity, part of the prosthesis is shown as transparent.
Figure 3:
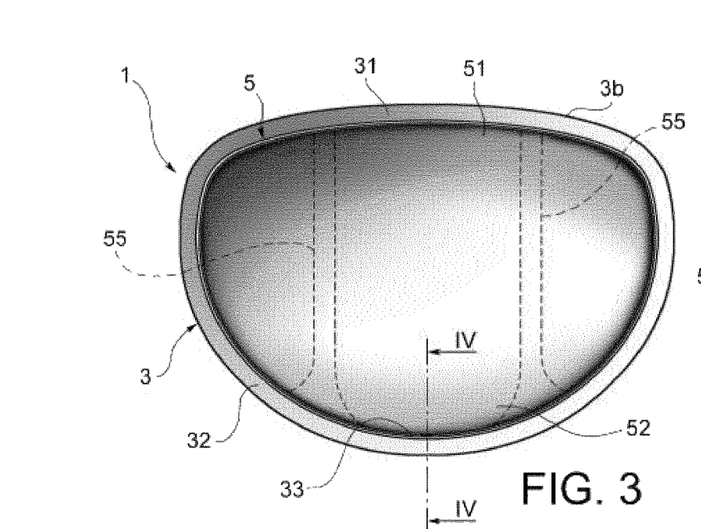
Figure 4:
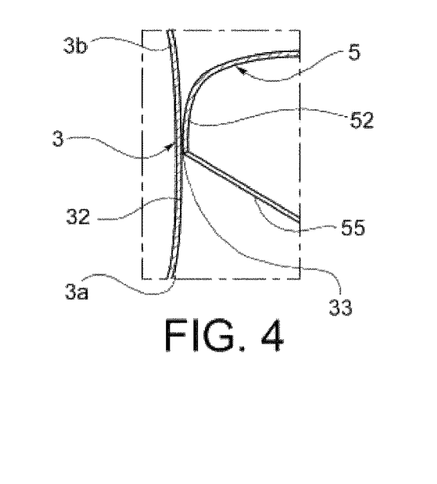
FIG. 4 is a sectional view of the valve prosthesis, taken along the line IV-IV in FIG. 3.

As can be seen in FIGS. 2 and 3, the free end 52 of the valve leaflet 5 is connected to the support wall portion 31 by at least one traction member 55 of flexible material (in the present example there are two of these members). The traction members 55 simulate the retaining/stopping function of the natural chordae tendineae, and are therefore dimensioned to such a length that the movement of the free end 52 of the valve leaflet is stopped at the coaptation surface 33.

The traction members 55 may be made of the same material as the valve leaflets 5 or of different material, and may be formed so as to resemble extensions from the free end 52 of the leaflet, or as separately made elements which are subsequently fixed to the free end of the valve leaflet.

The other ends of the traction members 55 are fixed to the supporting structure 3 on the side (the blood inflow side 3*a*) axially opposed to the side (the blood outflow side 3*b*) on which the valve leaflet is positioned. In order to connect the traction members to the supporting structure 3 and support them thereon, it is possible to provide post portions 35 projecting axially from the supporting structure 3 on the inflow side 3*a* of the valve prosthesis.

Preferably, predetermined areas (for example, areas adjacent to the commissural region) of the supporting structure 3 are provided with markers made of material opaque to radiation of predetermined wavelength, for example a radiopaque material such as a noble metal, for instance platinum or tantalum. The markers serve to facilitate the implantation of the prosthesis during a procedure making use of fluoroscopy, by providing a spatial reference to the operator, which is to be aligned with an anatomic reference.

Figure 5:
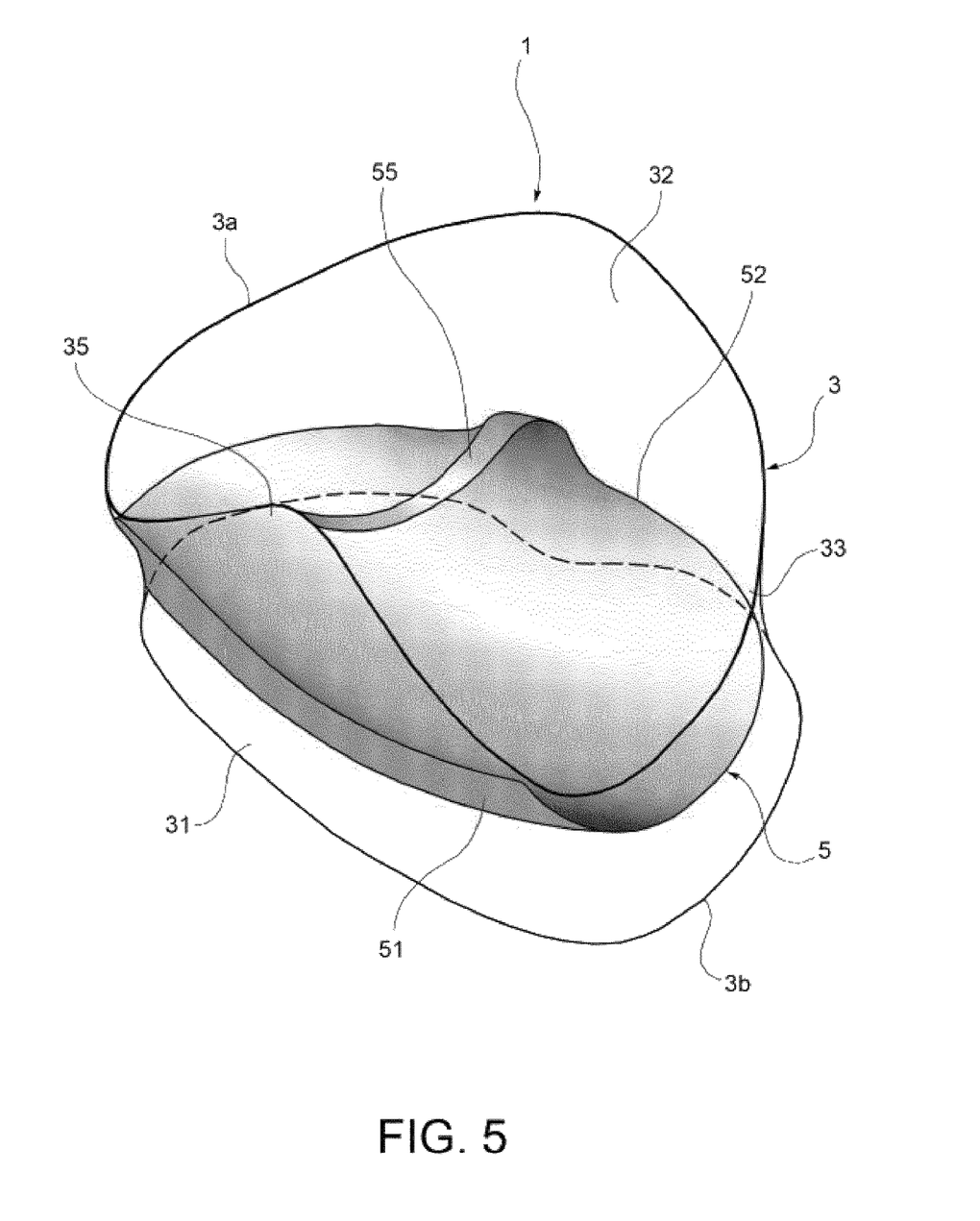
FIGS. 5 to 7 are perspective views from below of different embodiments of the valve prosthesis.

FIG. 5 shows another exemplary embodiment of a valve prosthesis according to the invention. Elements corresponding to those of the preceding embodiment have been given the same reference numerals; for a detailed explanation of these elements, reference should be made to the preceding part of the description.

The prosthesis of FIG. 5 differs from that of FIGS. 1 to 4 in that it has only one traction member 55 instead of a pair of traction members 55. Accordingly, the prosthesis of FIG. 5 has a single post portion 35, to which the end of the traction member 55 is connected.

More generally, the number of traction members 55 may vary according to circumstances; in an embodiment which is not illustrated, there is a plurality of traction members of different lengths, connected to a plurality of points distributed along the edge of the free end 52 of the valve leaflet 5. This arrangement enables the stresses acting on the valve leaflet 5 to be distributed uniformly. In a further embodiment which is not illustrated, there is a single traction member which forms an integral extension of the valve leaflet 5, and which therefore extends along the whole edge of the free end 52 of the valve leaflet 5. This configuration enables the distribution of stresses to be improved further.

Figure 6:
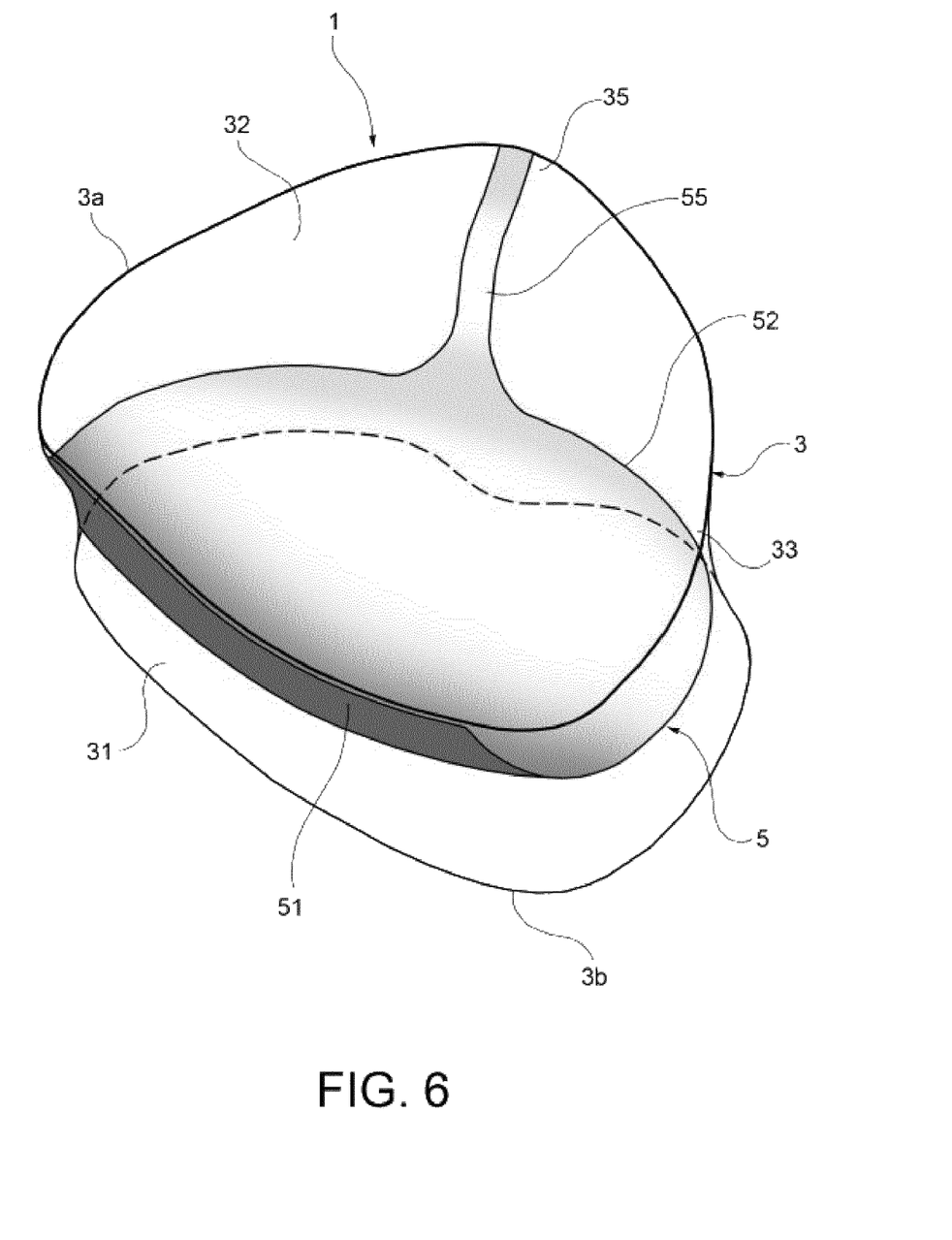

FIG. 6 shows a third exemplary embodiment of a valve prosthesis according to the invention. Elements corresponding to those of the preceding embodiments have been given the same reference numerals; for a detailed explanation of these elements, reference should be made to the preceding part of the description.

The prosthesis of FIG. 6 differs from that of FIG. 5 in that the traction member 55 is connected to the complementary wall portion 32, rather than to the support wall portion, in a position which is therefore diametrically opposite that shown in FIG. 5. Accordingly, the prosthesis of FIG. 6 has a post portion 35 positioned on the complementary wall portion 32, to which the end of the traction member 55 is connected.

Figure 7:
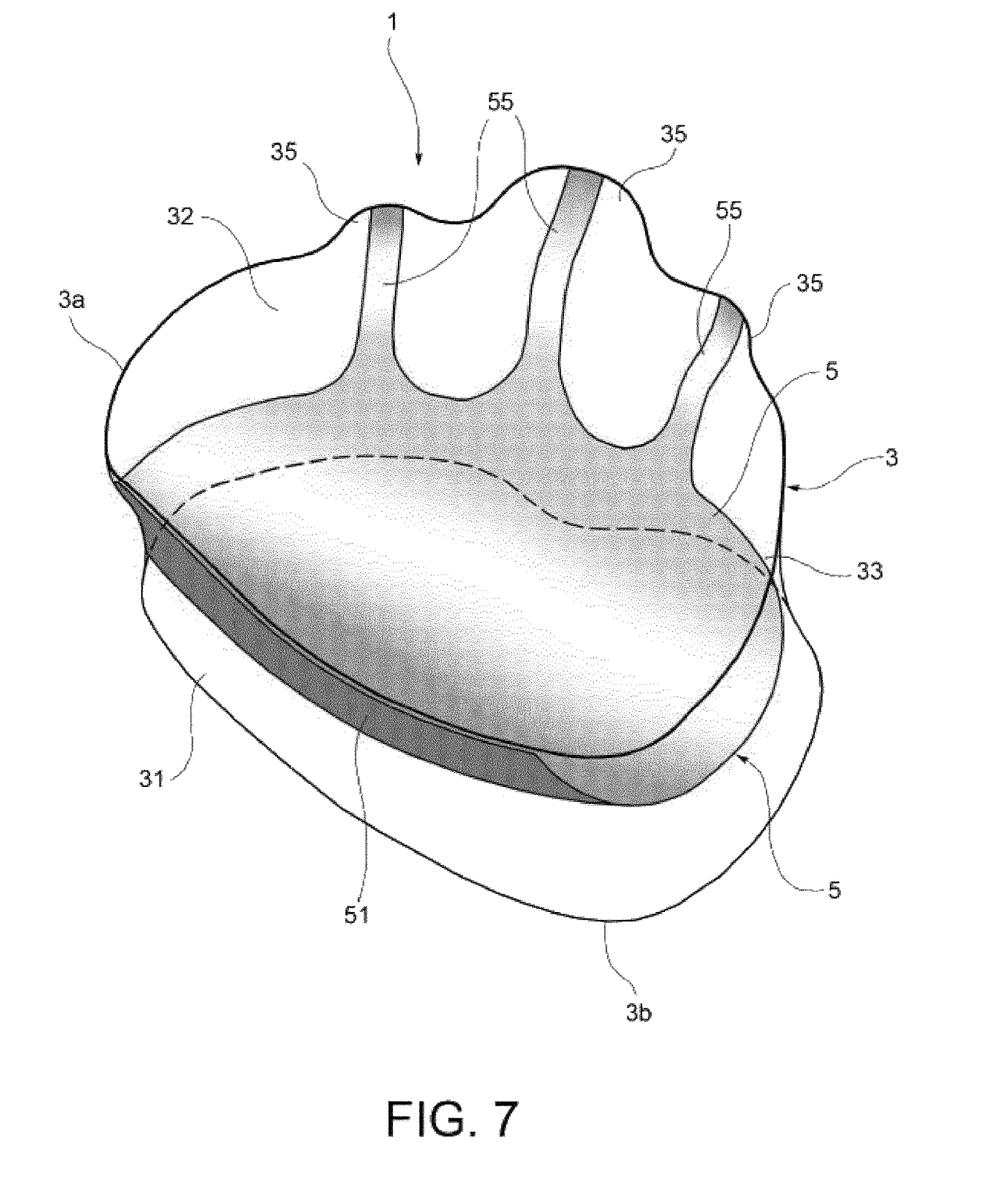

FIG. 7 shows a further exemplary embodiment of a valve prosthesis according to the invention. Elements corresponding to those of the preceding embodiments have been given the same reference numerals; for a detailed explanation of these elements, reference should be made to the preceding part of the description.

The prosthesis of FIG. 7 differs from that of FIG. 6 in that it has three traction members 55 instead of a single traction member 55. Accordingly, the prosthesis of FIG. 7 has three support portions 35, to which the ends of the traction members 55 are respectively connected.

Figure 8:
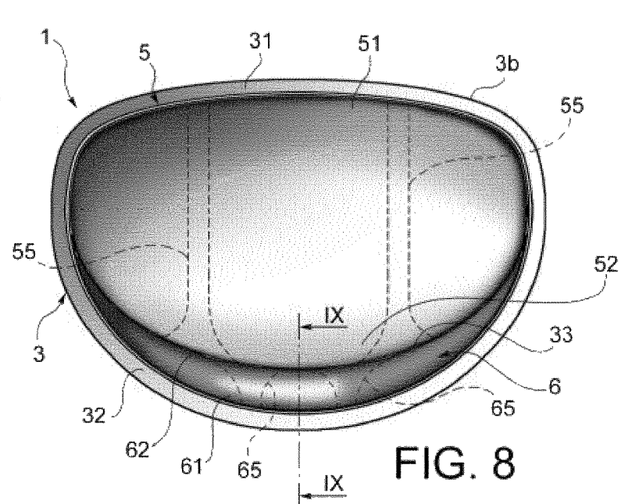
FIG. 8 is a plan view of a further valve prosthesis.
Figure 9:
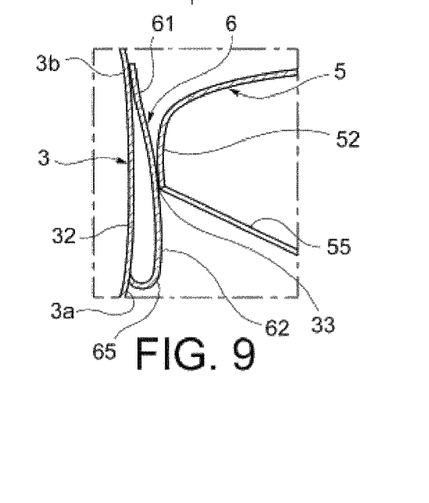
FIG. 9 is a sectional view of the valve prosthesis, taken along the line IX-IX in FIG. 8.

In a variant of the invention shown in FIGS. 8 and 9, the coaptation surface 33 is formed by a quasi-static coaptation leaf-let 6, positioned on the complementary wall 32 of the supporting structure 3. For the purposes of the present invention, the term "quasi-static" means that the coaptation leaflet 6 has a reduced mobility by comparison with the valve leaflet 3. The coaptation leaflet 6 comprises a root end 62 connected to the complementary wall portion 32 of the supporting structure 3. For this purpose, the outflow portion 3*a* of the valve stent has a valve support for the coaptation leaflet of the prosthesis. This support is integrated into the structure of the stent, and is designed to withstand cyclic fatigue stress, to provide adequate support for the coaptation leaflet, and to allow the prosthesis to be fully collapsed for insertion into the positioning system.

The coaptation leaflet 6 further comprises a free end 61 connected to the complementary wall portion 32 by means of at least one traction member 65 of flexible material, dimensioned to such a length that the coaptation leaflet 6 is kept bent towards the complementary wall portion 32. In order to connect the traction member 65 to the supporting structure 3 and support it thereon, it is possible to provide post portions projecting axially from the supporting structure 3 on the inflow side of the valve prosthesis. The number and extension of the traction members 65 of the coaptation leaflets may vary in a similar way to that described above with regard to the traction members 55 of the valve leaflet 5. In Variation the traction member 65 is arranged such that the free end 61 is pointing at an outflow end 3a. The materials from which the coaptation leaflet 6 is made are the same as those from which the valve leaflet 5 is made.

As can be seen in FIG. 8, the surface extension of the valve leaflet 5 is significantly greater than that of the coaptation leaflet 6. The anchoring line of the coaptation leaflet in the wall of the valve stent terminates in continuity with the anchoring line of the valve leaflet 5, forming two commissures in the antero-posterior position. The length of the anchoring line for the anterior leaflet (5) is typically around 40% of the annular circumference while the posterior leaflet (6) is the remaining 60%. The depth of the commissure must be at least 5-8 mm, similar to that of the rest of the coaptation surface 33.

As a general rule, the valve leaflet, and the coaptation leaflet if present, are preferably anchored directly to the valve stent at the inflow and to the post portions (at the outflow) by the interposition of biological or synthetic tissue. By means of this system, the shock of leaflet elongation during the systole/diastole phases can be absorbed jointly at the coaptation surface of the two leaflets, thus increasing the durability of the prosthesis over time.

Figure 10A:
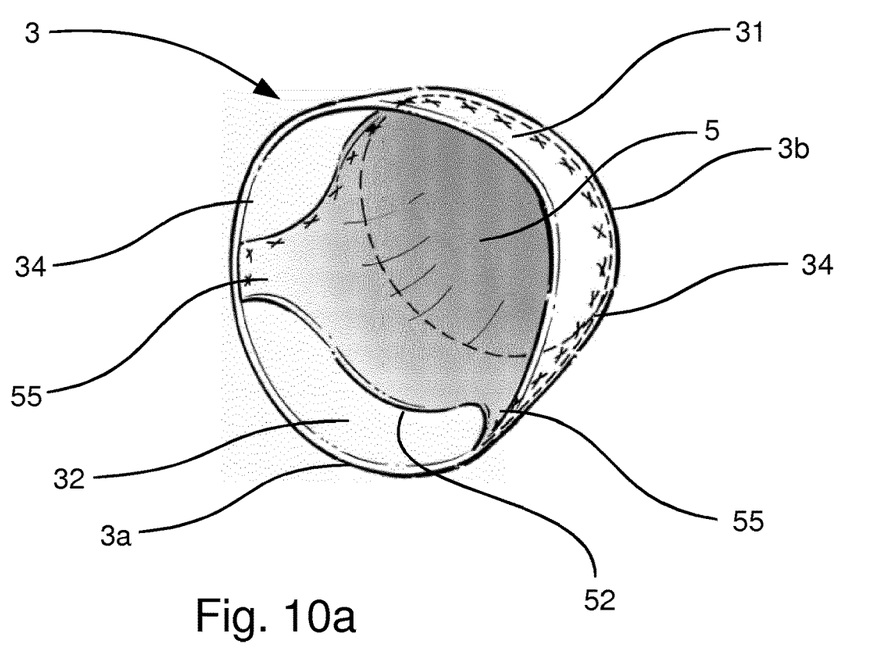
FIG. 10a is a perspective view from below (showing the outflow side) of the valve prosthesis in closed position.

FIG. 10a shows a perspective view of the support structure 3 from the outflow end 3a in a closed position. The closed position means that the valve leaflet 5 prevents a blood backflow through the support structure 3. The valve leaflet 5 and two traction members 55 are formed as a single piece made of pericardium. The leaflet 5 is stitched to the support wall portion 31 along schematically shown stitches. The free end 52 of the valve leaflet 5 is contacting the complementary wall portion 32 in the closed position. The traction members 55 are sewed at lateral portions 34 of the support structure 3 along schematically shown stitches. The traction members 55 prevent further movement of the valve leaflet 5 in the closed position, thereby securing a sealed closing.

Figure 10B:
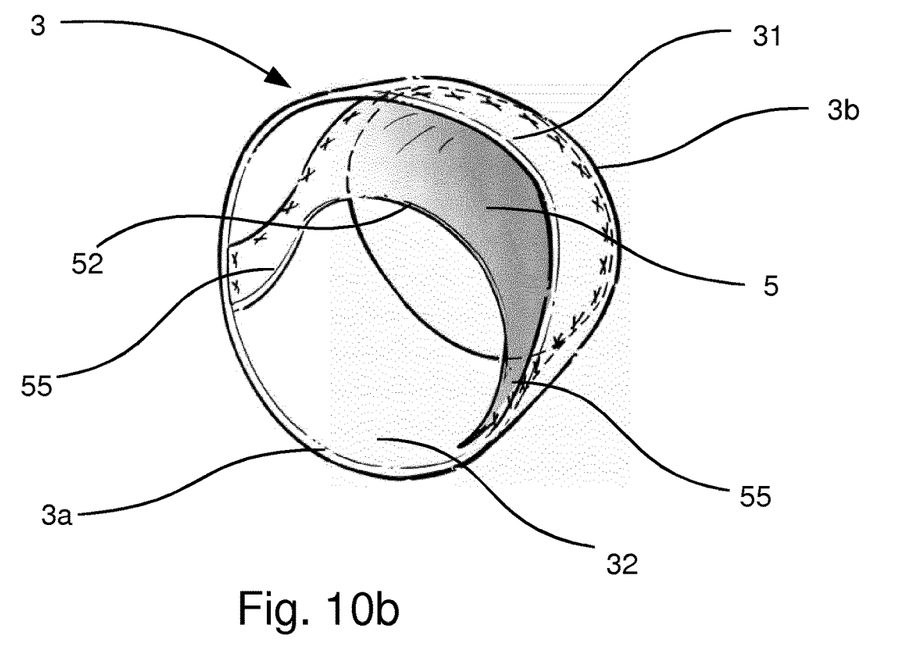
FIG. 10b is a perspective view from below (showing the outflow side) of the valve prosthesis in open position.

FIG. 10b shows a perspective view of the support structure 3 from the outflow end 3a in an open position. Open position means that the valve leaflet 5 does basically not interfere with the blood flow through the support structure 3 from the left atrium to the left ventricle during diastole. The free end 52 of the valve leaflet 5 is at distance to the complementary wall portion 32. Two traction members 55 are attached to lateral portions 34 and the free end 52 of the valve leaflet 5.

Figure 11A:
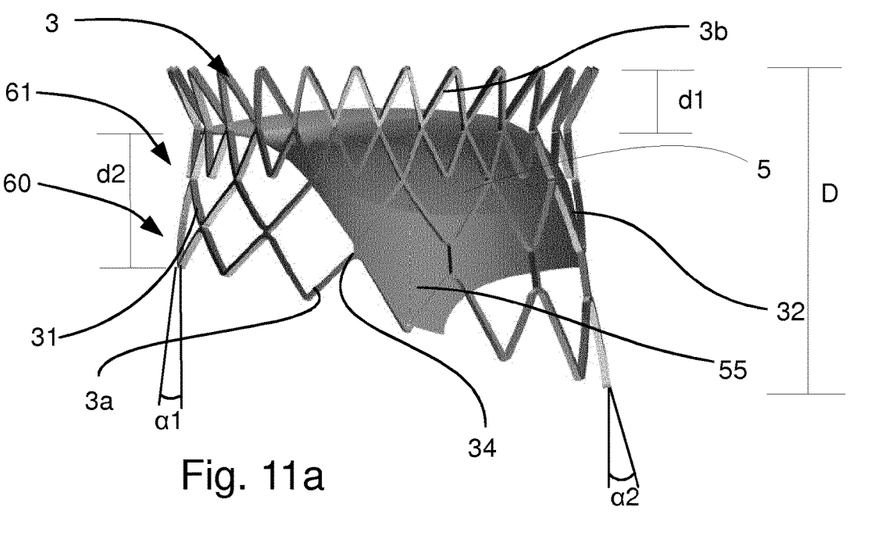
FIG. 11a is a side view of the valve prosthesis.

FIG. 11a shows a side view of the support structure 3 with the valve leaflet 5 mounted inside the support structure 3. The valve leaflet 5 is sewed to the lateral portions 34 by means of the traction members 55 along the schematically shown stitches. The inflow end 3b has a flare of 10° with respect to the blood flow direction. The outflow end 3a has a flare of 30° with respect to the blood flow direction. The axial length d1 of the inflow end 3b is shorter than the shortest axial length d2 of the outflow end 3a. The flare of the outflow end 3a is in a curvilinear manner. There is a outwardly flared portion 61 and a slightly inwardly bend portion 60, with respect to the blood flow direction. The flares might also be present in a more curvilinear manner. Further, the flares are asymmetrically arranged. The anterior portion corresponding to the supplementary wall portion 31 is flared in an angle α1. α1 is smaller than an angle α2 present in the flare of the posterior portion corresponding to the complementary wall portion 32.

The support structure comprises multiple struts which form cells. The struts have a width of 500 µm. A wall thickness of the support structure 3 is also 500 µm. The support structure has an axial length D of about 32 mm from the inflow end 3b to the outflow end 3a measured on the support wall portion 31. The cells on the outflow end 3a can have a larger dimension than the cells on the inflow end 3b. An anterior portion corresponding to the supplementary wall portion 31 in FIG. 11a is shorter in axial direction than a posterior portion corresponding to the complementary wall portion 32. The lateral portions 34 connect the anterior portion and the posterior portion such that the lateral portions gain constant in length from the anterior portion to the posterior portion. The support structure might be formed out of Nitinol.

Figure 11B:
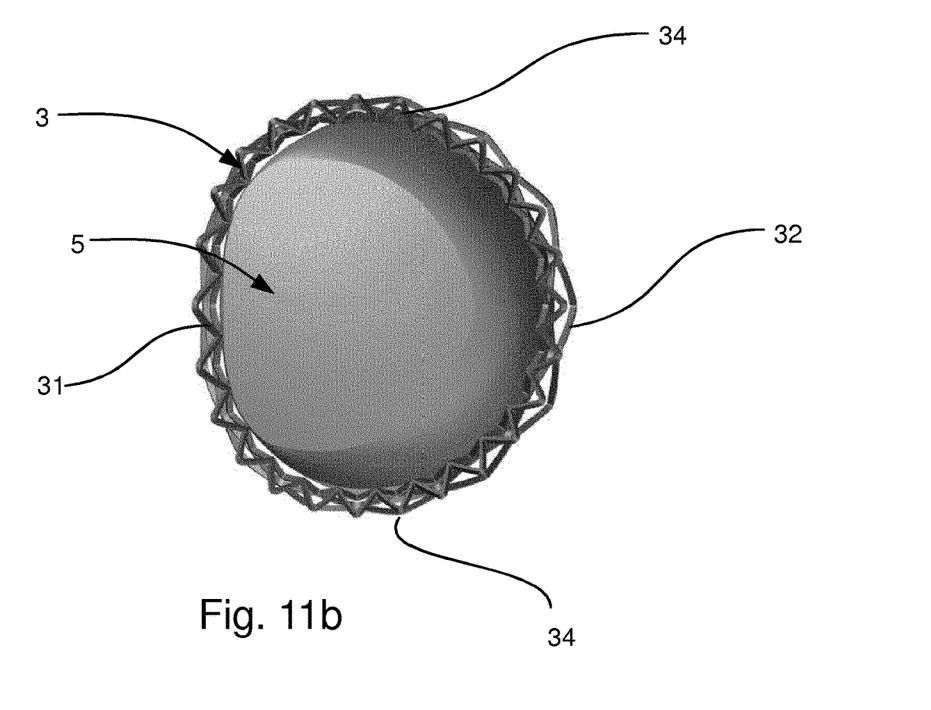
FIG. 11b is a top view (inflow view) of the valve prosthesis.

FIG. 11b shows a top view of the support structure 3 housing the valve leaflet 5. The support structure is in a D shape. The D shape is arranged such that the anterior portion corresponding to the support wall portion 31 in FIG. 11b is only slightly convexly bent and the posterior portion corresponding to the complementary wall portion 32 is convexly bent with a smaller radius of curvature. The distance between the lateral portions 34 is 1.2 times as big as the distance between the anterior portion and the posterior portion.

The invention claimed is:

1. An atrio-ventricular valve prosthesis comprising:
   a ring-shaped supporting structure to be anchored at the valve annulus; and
   a single extended valve leaflet having a free end and a root end, made of flexible material floatingly supported by the supporting structure allowing for a movement of the free end within the supporting structure,
   wherein the supporting structure includes,
      a support wall portion at which the root end of the valve leaflet is connected, and
      a complementary wall portion opposite to the support wall portion having a coaptation surface configured to be sealingly engaged with the free end of the valve leaflet, and extending in a direction substantially parallel to a movement direction of the free end of the valve leaflet at the coaptation surface,
   wherein the free end of the valve leaflet is connected to the support wall portion or to the complementary wall portion by a traction member of flexible material having a length that the movement of the free end of the valve leaflet is stopped at the coaptation surface.

2. The prosthesis according to claim 1, wherein the coaptation surface extends in the direction parallel to the movement direction of the free end of the valve leaflet for a width (h) of at least 5 mm.

3. The prosthesis according to claim 1, wherein the coaptation surface is formed by an inner face of the complementary wall portion of the supporting structure.

4. The prosthesis according to claim 1, wherein the coaptation surface is formed by a quasi-static coaptation leaflet which comprises a root end connected to the complementary wall portion, and a free end connected to the support wall portion or to the complementary wall portion by the traction member of flexible material which is dimensioned to such a length that the coaptation leaflet is kept bent towards the complementary wall portion.

5. The prosthesis according to claim 1, wherein the supporting structure comprises a skeleton forming a valve stent, configured to assume a delivery configuration when the stent is collapsed, and an implantation configuration when the stent is expanded.

6. The prosthesis according to claim 1, wherein the supporting structure is configured for a sutureless implantation on the valve annulus.

7. The prosthesis according to claim 1, wherein the traction member is connected to a post portion of the support wall portion or the complementary wall portion, the post portion axially protruding from a blood outflow side of the supporting structure.

8. The prosthesis according to claim 1, wherein at least one predetermined area of the supporting structure is provided with a positioning marker of material opaque to radiation of a predetermined wavelength.

9. The prosthesis according to claim 1, wherein there are a plurality of the traction members having different lengths that are connected to a plurality of sites distributed along the edge of the free end of the valve leaflet.

10. The prosthesis according to claim 1, wherein the traction member constitutes an integral extension of the valve leaflet, and extends transversely along the entire edge of the free end of the valve leaflet.

11. The prosthesis according to claim 1, wherein the valve and the traction member are constructed as a single piece.

12. The prosthesis according to claim 1, wherein the valve and the traction member are constructed as a single piece made of pericardium.

13. The prosthesis according to claim 1, wherein the traction member is attached to lateral portions of the supporting structure.

14. The prosthesis according to claim 1, wherein ends of the supporting structure are flared outwardly with respect to a blood flow direction.

15. The prosthesis according to claim 14, wherein the flared ends are flared differently such that an inflow end is flared with a wider angle with respect to the blood flow direction than an outflow end.

16. The delivery device comprising a prosthesis according to claim 1.

17. The prosthesis according to claim 1, wherein the supporting structure has a D-shaped cross section in the area where the valve leaflet is contacting the structure.

18. The prosthesis according to claim 17, wherein the straight part of the D shape is the support wall portion or the complementary wall portion and the bent part of the D shape is the other wall portion, complementary wall portion or support wall portion, respectively.

19. The prosthesis according to claim 18, wherein the coaptation surface is arranged at an arc-shaped side of the D-shaped cross section of the supporting structure.

20. The prosthesis according to claim 18, wherein traction member reaches up to an edge of the supporting structure.

21. The prosthesis according to claim 1, wherein the ring-shaped supporting structure includes flares at an inflow end and flares at an outflow end, wherein the flares at an inflow end and the flares at an outflow end are asymmetrically arranged.

* * * * *